United States Patent [19]

Teringo

[11] Patent Number: 5,026,345
[45] Date of Patent: Jun. 25, 1991

[54] NON-MECHANICAL INCAPACITATION SYRINGE SAFETY NEEDLE GUARD

[76] Inventor: William Teringo, 201 Country Club Dr., SW., Leesburg, Va. 22075

[21] Appl. No.: 510,916

[22] Filed: Apr. 18, 1990

[51] Int. Cl.$^5$ .............................................. A61M 5/00
[52] U.S. Cl. .................................... 604/110; 604/192; 604/263
[58] Field of Search ................. 604/110, 187, 192, 263

[56] References Cited

U.S. PATENT DOCUMENTS

| | | |
|---|---|---|
| 3,890,971 | 6/1975 | Leeson et al. . |
| 3,951,146 | 4/1976 | Chiquiar-Arias . |
| 4,248,246 | 2/1981 | Ikeda . |
| 4,270,536 | 6/1981 | Lemelson ............................ 604/192 |
| 4,710,170 | 12/1987 | Haber et al. ........................ 604/110 |
| 4,725,267 | 2/1988 | Vailancourt . |
| 4,728,321 | 3/1988 | Chen .................................... 604/110 |
| 4,735,311 | 4/1988 | Lowe et al. . |
| 4,738,663 | 4/1988 | Bogan . |
| 4,755,170 | 7/1988 | Golden . |
| 4,775,369 | 10/1988 | Schwartz . |
| 4,778,453 | 10/1988 | Lopez . |
| 4,799,927 | 1/1989 | Davis et al. . |
| 4,801,295 | 1/1989 | Spencer . |
| 4,816,024 | 3/1989 | Sitar et al. . |
| 4,872,552 | 10/1989 | Unger . |
| 4,880,413 | 11/1989 | Giuffre et al. . |

*Primary Examiner*—John D. Yasko
*Attorney, Agent, or Firm*—Pennie & Edmonds

[57] ABSTRACT

This invention relates to a non-mechanical locking incapacitation syringe safety needle guard for preventing reuse of a syringe and needle assembly and for preventing an accidental needle injury. The needle guard has a hollow chamber filled with liquid adhesive. When the needle portion, luer lock, and neck of the syringe are placed in the chamber, the adhesive locks the needle guard permanently to the syringe, thereby disabling the needle portion. Further, the adhesive is drawn into the syringe chamber to lock the plunger of the syringe to the syringe, thereby immobilizing the plunger. This renders the syringe and the needle completely useless.

18 Claims, 3 Drawing Sheets

NON-MECHANICAL INCAPACITATION SYRINGE SAFETY NEEDLE GUARD

BACKGROUND OF THE INVENTION

1. FIELD OF THE INVENTION

This invention relates to a safety needle guard for preventing inadvertent needle punctures or sticks and for rendering a syringe and needle assembly useless after one use by permanently fixing the plunger in the syringe body and capping the entire needle with the needle guard, by use of a fast acting adhesive contained in the needle guard.

2. BACKGROUND OF THE PRIOR INVENTION

In light of widespread abuse of syringes and needles by drug addicts and the recent spread of AIDS associated with the use of contaminated needles, the prior inventions proposed a syringe and needle assembly with various safety features. To prevent reuse of discarded disposable syringe and needle assemblies and for preventing inadvertent needle punctures, many types of safety devices have been proposed, for example, in U.S. Pat. No. 4,270,536 to Lemelson, U.S. Pat. No. 4,248,246 to Ikeda, U.S. Pat. No. 4,710,170 to Haber et al., U.S. Pat. No. 4,270,536 to Chen, U.S. Pat. No. 4,735,311 to Lowe et al., U.S. Pat. No. 4,801,295 to Spenser, and U.S. Pat. No. 4,872,552 to Unger.

U.S. Pat. No. 4,270,536 to Lemelson discloses a needle breaking device. Specifically, after using the syringe and needle assembly, a plunger portion of the syringe is taken completely out of the syringe. The head of the plunger has a hole for holding the needle in place during breakage. However, this method or device is not safe, in that, the fluid contained within the needle, which may be contaminated, becomes exposed to the person handling the syringe when the plunger is completely pulled out. Moreover, during the breaking process, the needle of the syringe may shatter, generating fragments which can stick the user and expose the user to potentially biohazardous material.

A second embodiment of the Lemelson patent discloses a sheath for encapsulating the needle by taking the plunger off the syringe and placing it over the needle. Again, because, the plunger has to be taken off the syringe, contaminated fluid in the needle can expose the user. Furthermore, this device does not disable the syringe as the plunger can be placed back into the syringe.

U.S. Pat. No. 4,248,246 to Ikeda discloses a cap for enclosing a needle portion of a sampling blood collector. The cap contains a seal material which is placed over the tip of the needle after its use. However, Ikeda does not offer sufficient protection against subsequent accidents because the cap can be easily pulled off.

U.S. Pat. No. 4,735,311 to Lowe et al. (Lowe) is substantially similar to the Ikeda patent, except that the Lowe patent relates to a syringe. A cap is used in the identical manner as the Ikeda patent to seal the needle and to prevent an inadvertent needle puncture.

U.S. Pat. No. 4,710,170 to Haber et al (Haber) discloses a syringe assembly for preventing an accidental needle puncture and for rendering the syringe inoperative. Specifically, the entire needle assembly can be pulled into the syringe body. The plunger is then pushed directly into the needle portion until the needle completely embeds into the plunger. While this device completely disables the syringe and prevents an accidental needle puncture once disabled, the shortcoming of this patent is that it cannot be used in conventional syringe and needle assemblies. On the other hand, the present invention is related to a protective sheath which can be used on any conventional assembly by simply capping the needle with the sheath as opposed to the elaborate steps required in the Haber patent. Also, the steps required in the Haber patent to disable the syringe may in some instances be too complicated for ordinary individuals to follow.

U.S. Pat. No. 4,728,321 to Chen discloses a syringe cap for disabling the syringe after one use. Specifically, a plug at the tip of the cap is slidable along the inner surface of the cap. By pushing in the plug, the needle will engage the tip portion of the needle to puncture the plug. Then, pulling the plunger causes adhesive contained within the plug to flow into the needle, thereby disabling the needle when the adhesive sets. The Chen patent has two drawbacks. First, the plug is easily pushed into the needle. Even a slight inadvertent push can cause the plug to engage the needle. The Chen patent provides no adequate measures for preventing the plug from being engaged accidentally. Second, the entire cap along with the plug can be pulled off, thereby exposing the needle for a possible needle injury Further, the Chen patent does not provide any means for disabling the syringe portion U.S. Pat. No. 4,801,295 to Spenser discloses a sleeve which slides along the outer body syringe surface. When the sleeve is fully extended the needle is shielded, thereby avoiding an accidental needle puncture. While the sleeve is designed to be permanently locked in the extended safety position, as shown in FIGS. 6 and 18, the safety sleeve can be broken with force or can be severed from the syringe, thereby exposing the entire needle. Because the syringe and the needle are not disabled, the syringe and the needle can be reused.

U.S Pat. No. 4,872,552 to Unger discloses a safety cap which is hinged to a syringe and needle assembly. When using the assembly, the cap is first pivoted away from the needle portion. After using the assembly, the cap is placed back on the needle portion. The cap also includes a block slidably engaged therewith to enable the tip portion of the needle to penetrate the block, thus shielding the needle to prevent an accidental needle puncture. However, the shortcoming of the Unger invention is that the assembly is not disabled. Any one can remove the cap from the assembly and reuse the assembly.

Currently, used syringes and needles are first collected in mass quantities. Once collected they are destroyed or disposed of by one or several methods. For instance, needle chopper, autoclaving (deforming), and incineration have been used to destroy or dispose used syringes and needles. However, these methods are not entirely satisfactory, in that, the syringe and needle assemblies are not rendered useless immediately after their use. This provides an opportunity for individuals to pilfer syringes and needles during the collection of these discarded items. By providing a needle guard in the present invention to permanently and immediately render the syringe and needle useless, even if the discarded and disabled syringes and needles are pilfered during the collection for destruction, they cannot be reused.

The prior inventions do not provide a non-mechanical device for immediately rendering the syringe and needle completely inoperative by using adhesive in the needle guard. Rather, the prior inventions require a safety device to be part of the original needle assembly package and they are either of a mechanical locking nature or require force to break the needle portion of the syringe. None of the prior inventions encompasses the entire range of safety and permanence of the present invention which completely renders all functional parts of syringe inoperative.

SUMMARY OF THE INVENTION

The present invention comprises a needle guard similar to a conventional needle guard. However, in the present invention, the needle guard contains fast curing colored liquid adhesive. A penetratable membrane that prevents flow and premature drying of the adhesive is inserted and secured within the needle guard. To use the present needle guard, the needle portion of the syringe after its use is immediately inserted into the needle guard and the syringe plunger is pulled back and then pushed forward. The action of inserting the needle breaks the membrane, lodging the luer lock past the membrane when fully inserted and drawing the adhesive to the outer surface of the luer lock. The action of pulling back the syringe plunger causes the adhesive to flow through the needle and into the space in the luer lock and into the syringe body, the flow of the adhesive being clearly visible due to the colored adhesive It should be noted that the colored adhesive is preferred, but not required because even clear adhesive is visible in the syringe. When the adhesive fills the syringe body enough to fix the plunger to the body, the plunger is pushed forward to bring the rubber plunger tip in contact with the adhesive in the body. Note that the amount of adhesive in the guard is enough to accomplish the above noted objective. The end result is that the adhesive permanently adheres the needle guard to the exterior surface of the syringe luer lock, the luer lock to the syringe body, and the plunger to the syringe body while filling the space in the needle with the adhesive. All component parts of the syringe assembly are adhered permanently together with the space in the needle completely filled, rendering the syringe and needle assembly completely inoperative and incapable of causing injury.

The curing process of the adhesive begins immediately, with the cap being secured over the needle and resistant to removal within seconds. The adhesive is completely set in normally less than thirty minutes. However, the syringe and needle assembly is rendered inoperative immediately from the moment the adhesive is applied since removal of adhesive during the brief curing period requires equipments and solvents which would destroy the syringe plastic. This makes the removal of adhesive from the syringe and needle assembly impractical.

The present invention comprises two embodiments. In the first embodiment, the needle guard is completely separate from the syringe and needle assembly. In other words, the needle guard may be separately packaged. This enables the needle guard to be used with any conventional disposable syringe and needle assembly. One advantage of this embodiment is that sterilization of the needle guard is not required. This factor is of particular importance since if sterilization were required the adhesive would require sterilization also. This would result in an increased cost, current sterilization methods might adversely affect the stability of the adhesive.

In the second embodiment, a single unit contains two chambers, one being the shipping needle guard and the other being the adhesive filled needle guard. The shipping needle guard portion of the unit, consisting of the one chamber without adhesive, is placed on the needle portion of the assembly at time of manufacture. After using the syringe, the combination unit is inverted and another chamber with adhesive in the needle guard is placed on the needle as applied in the first embodiment. In this embodiment, the needle guard serves two purposes, one for guarding the needle portion before using and another for guarding and disabling the syringe and needle assembly after using.

Accordingly, the object of the invention is to provide a needle guard for a syringe and needle assembly to prevent an inadvertent needle puncture and for rendering the assembly completely inoperable immediately thereafter using.

Another object of the invention is to provide a needle guard, which does not require sterilization, for use with any conventional disposable syringe and needle assembly.

Another object of the invention is to provide a needle guard supplied with a syringe and needle assembly where the needle guard serves two functions, one to serve as a conventional needle guard and another to serve as a syringe and needle assembly immobilizer.

The foregoing invention and features and advantages of my invention will be better appreciated from the following description.

DETAILED DESCRIPTION OF THE DRAWINGS

Figure 1:
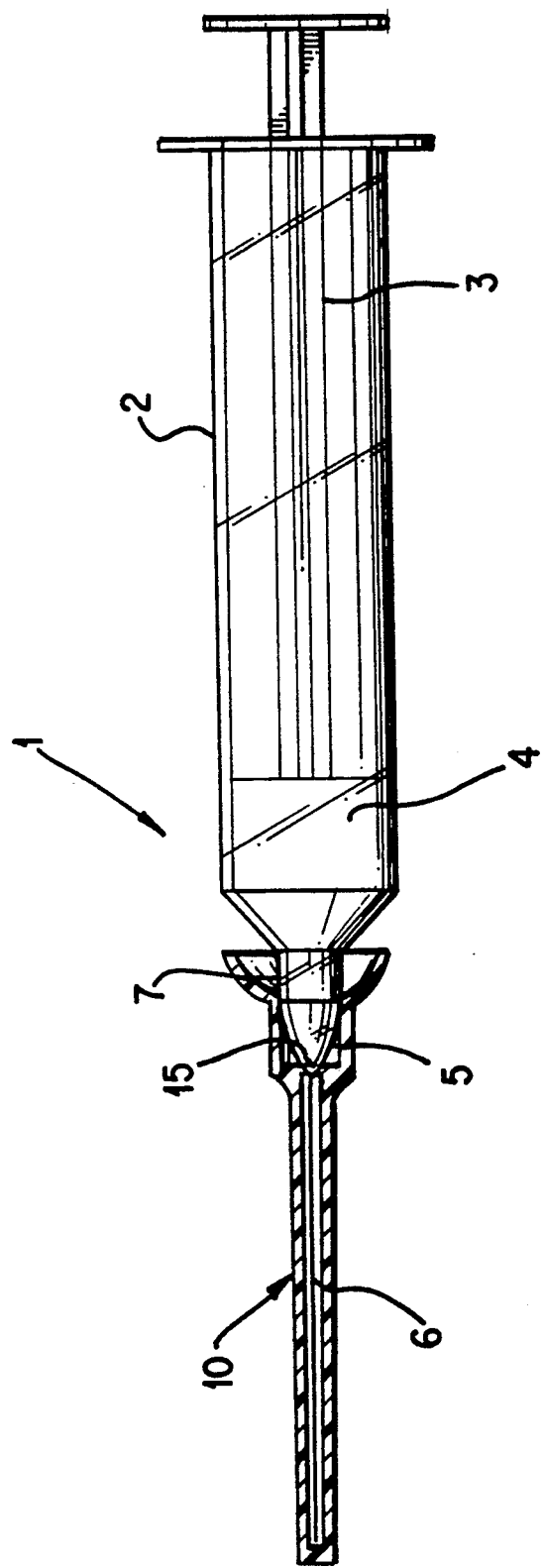
FIG. 1 shows a syringe and needle assembly with a needle guard of the first embodiment.

FIG. 1 shows a conventional syringe and needle assembly (1) with a needle guard (10) of the present invention placed on a needle portion (6) of the assembly (1). The conventional syringe assembly includes a syringe body (2), a plunger (3) with a plunger rubber tip (4), a luer lock (5) where the needle (6) joins the syringe neck (7).

Figure 2:
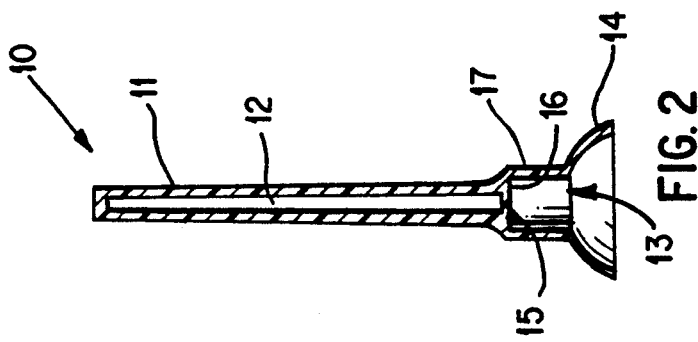
FIG. 2 is a front elevational view of the needle guard of the first embodiment.

FIG. 2 shows the needle guard (10) of the first embodiment, comprising a sheath (11) with the space within the sheath (11) filled with adhesive (12). One type of adhesive which can be used in the present invention is cyanoacrylate, which has a fast curing time. Further, the adhesive is preferably, but necessarily, colored to visibly show the adhesive flows when the assembly is capped with the needle guard. Furthermore, the adhesive can be made so that the color changes when the shelf life of the adhesive expires. In other words since the adhesive could deteriorate with age, the color change would indicate that the needle guard might be ineffective and thus should be discarded. This can be done by a conventional means.

The needle guard further comprises a lip (16) for seating a sealing membrane (15). The membrane (15) seals the adhesive in the sheath (11) for preventing premature curing and for preventing the adhesive from flowing out of the sheath (11). The membrane can be made from any conventional sealing material which does not react with the adhesive used therein such as plastic, aluminum foil, rubber, or laminated material. A luer lock and neck engaging area (13) conforms with the shape of a conventional luer lock and syringe neck exterior shape of the syringe assembly. The opening end of the needle guard has an enlarged flange (14) for guiding the needle (6) and for preventing a needle puncture to the user's hands due to stress situations or inattentiveness of the user.

Figure 3:
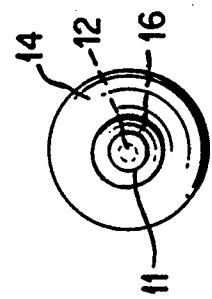
FIG. 3 is a top view of the needle guard of FIG. 2.

FIG. 3 shows a top view of the needle guard (10). As is clearly shown, the sheath (11), lip (15), and flange (14) are concentrically circular in cross section. However, the present invention does not require the shape of the needle guard to have a circular cross section as it can have any shape without deviating from the spirit of the invention.

In use, fingers engage therebetween an engaging area (17) and the flange (14), and the needle portion is guided into the sheath (12). The needle portion (6) punctures the seal membrane (15) and is inserted into the sheath, lodging the luer lock (5) of the syringe assembly (1) past the membrane (15). This insertion causes the adhesive to flow out to the luer lock (5) and the neck (7) areas, thereby locking the luer lock (5) and the neck (7) to the needle guard when the adhesive cures. Immediately thereafter, the plunger is pulled back to draw adhesive into the needle and into the syringe chamber. Then, the plunger is pushed forward to bring the plunger rubber tip (4) in contact with the adhesive in the chamber. The end result is that the adhesive permanently adheres the needle guard to the exterior surface of the luer lock 95), the luer lock to syringe body (2) and the plunger rubber tip (4) to the body (2) while filling the needle with adhesive. All component parts of the syringe assembly (1) are rendered completely useless by the adhesive.

Figure 4:
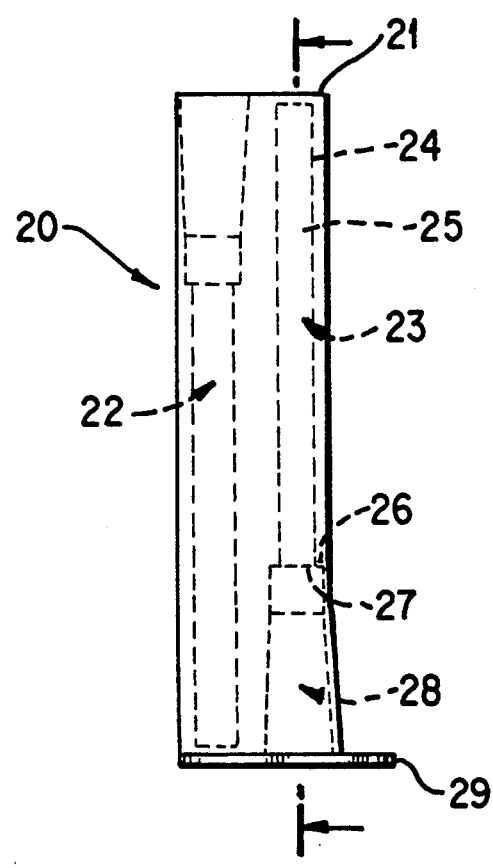
FIG. 4 is a front elevational view of the needle guard of the second embodiment.

The second embodiment of the invention is shown in FIGS. 4–8. In FIG. 4, the needle guard (20) comprises a rectangular sheath (21) with two similar hollow chambers (22, 23), the only difference in the chambers being that one (23) of the chambers (22, 23) contains colored adhesive and a sealing membrane (27). Therefore, it is to be noted that only the chamber (23) with the adhesive and sealing membrane (27) need be described. Like the first embodiment, the chamber (23) has a sheath (24) filled with colored adhesive. Note, however, that the coloring is not necessary as explained before. A shoulder (26) permits the sealing membrane (27) to be seated therein to seal in the adhesive and to prevent the adhesive from prematurely curing.

A luer lock and syringe neck engaging area (28) conforms with the shape of a conventional luer lock and syringe neck shape of the syringe assembly (1) which enables the adhesive to flow therebetween. The opening end of the locking sheath (24) has an enlarged flange (29) for guiding the needle (6) and for preventing a needle puncture.

Figure 6:
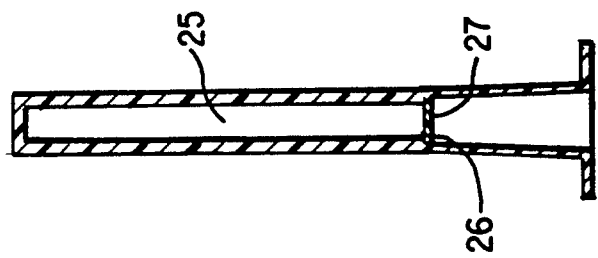
FIG. 6 is a cross sectional view as indicated by A—A in FIG. 4.
Figure 8:
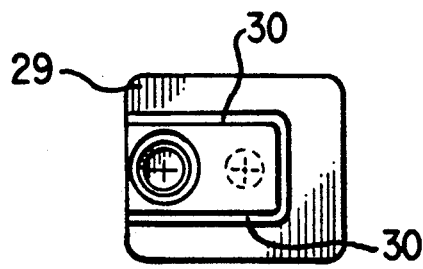
FIG. 8 is a top view of the needle guard of FIG. 4.
Figure 5:
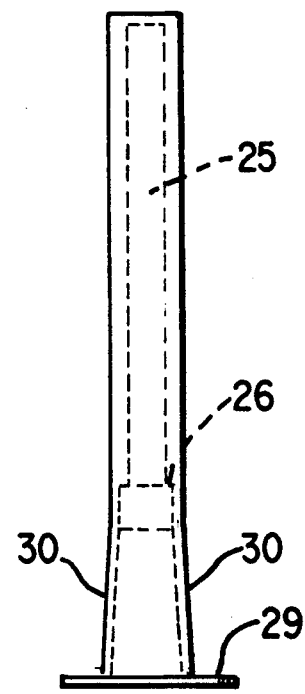
FIG. 5 is a side elevational view of the needle guard of FIG. 4.
Figure 7:
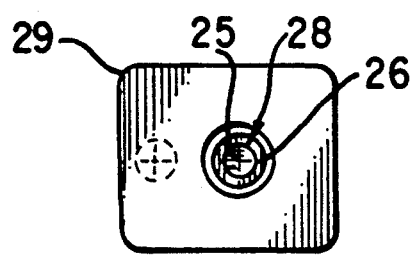
FIG. 7 is a bottom view of the needle guard of FIG. 4.

FIGS. 5 shows a side view and FIG. 6 shows a cross sectional view of the chamber (25) with the shoulder (26) shown clearly. FIG. 7 shows a bottom view of FIG. 4 wherein the chamber (25), the shoulder (26), the luer lock and syringe neck engaging area (28) are shown as being concentrically structured. FIG. 8 shows a top view of FIG. 4 whereby the nonlocking sheath (22) is shown.

In use, the needle guard (20) is first removed from the syringe assembly prior to its use. Specifically, one sheath (22) comes engaged with the needle portion, luer lock, and neck of the syringe. After the syringe has been used, the needle guard with the locking sheath is to be placed over the used syringe and needle assembly. Specifically, the guard is inverted with the finger engaging area (30) engaged between fingers and the flange (29) also engaged between the same fingers. The needle portion (6), luer lock (5) and neck (7) are guided into the locking sheath as described in the first embodiment above.

The foregoing description is only illustrative of the principle of my invention. It is to be understood that the invention is not limited to the exact construction as illustrated and described herein. Accordingly, all expedient modifications may be made within the spirit of my invention.

I claim:

1. A non-mechanical locking syringe safety needle guard means for incapacitating a syringe assembly having a luer lock attached to a discharge end thereof and a hypodermic needle attached to said luer lock, said needle guard comprising:
   an elongated sheath means having a chamber for encapsulating the entire needle and said luer lock, said chamber containing adhesive therein; and
   means for sealing said adhesive within said chamber, whereby said adhesive incapacitates said syringe assembly and bonds said entire needle and said luer lock to said needle guard when said needle portion is fully inserted into said sheath means.

2. A needle guard means according to claim 1, wherein said sealing means being disabled by a disabling means to permit said assembly access to said adhesive.

3. A needle guard means according to claim 2, wherein said disabling means comprises said needle, said needle puncturing said sealing means.

4. A non-mechanical locking syringe safety needle guard means for incapacitating a syringe assembly having a syringe body, a plunger operating within said body, a neck integral with a discharge end of said body, a luer lock attached to said neck, and a hypodermic needle attached to said luer lock, wherein said guard means comprises:
   a permanent elongated sheath means having an elongated chamber with an opening end, said chamber containing adhesive;
   a sealing means for sealing said opening end to contain and seal said adhesive therein; and
   a luer lock and syringe neck engaging means being integral with said sheath means at said opening end, said engaging means adapted to engage said luer lock and said neck of said assembly;
   wherein, said guard means being adapted to be inserted to first engage said sealing means with said needle to thereby break said sealing means, said guard means being further inserted to permit said luer lock and said neck to engage said engaging means, said sheath means and said engaging means permitting said adhesive to flow into said engaging means when said assembly is fully inserted into said guard, said adhesive bonding said guard means to the entire needle and said luer lock when said adhesive cures, rendering said assembly immediately inoperative and also preventing an inadvertent needle puncture.

5. A needle guard means according to claim 4, wherein said assembly is completely rendered inoperative by pulling said plunger to draw adhesive in the chamber immediately after capping said guard means on the needle, luer lock, and neck of the assembly, said plunger being pushed thereafter to contact said plunger with said adhesive, whereby said adhesive permanently adhering said needle guard means to the exterior surface of said luer lock and said neck, said luer lock to said neck, and said plunger to said syringe body while filling the space in said needle with said adhesive, thereby permanently adhering all operative parts of said assembly to render said assembly completely inoperative.

6. A needle guard means according to claim 4 or 5, wherein said sheath means further comprising an enlarged flange means adjacent said engaging means for preventing an accidental needle puncture to the user's hand when manually inserting said needle to said guard means.

7. A needle guard means according to claim 4 or 5, wherein said adhesive is colored to visually indicate flow of said adhesive.

8. A needle guard means according to claim 6, wherein said adhesive is colored to visually indicate flow of said adhesive.

9. A needle guard means according to claim 4 or 5, wherein said engaging means having a lip means adjacent said opening end for seating said sealing means thereon.

10. A needle guard means according to claim 4, wherein said guard means further having a removable sheath means for capping said needle, said luer lock and said neck prior to capping said permanent sheath means.

11. A needle guard means according to claim 4, wherein said removable sheath means and
said permanent sheath means being integral and juxtaposed side-by-side so that the opening end for each sheath means faces in the opposite directions.

12. In a syringe and needle assembly comprising a syringe body, a plunger operating within said body, a neck integral with a discharge end of said body, a luer lock attached to said neck, and a hypodermic needle attached to said luer lock, and a safety needle guard means for protecting the needle and luer lock of the assembly, the improvement wherein said guard means comprising:
two elongated sheath means each having an elongated chamber with an opening end;
one of the two chambers containing adhesive;
a sealing means for sealing the opening end of said one chamber to contain and seal said adhesive therein;
each sheath means having a luer lock and syringe neck engaging means adjacent said opening end and integral to said sheath means, said engaging means being adapted to engage said luer lock and said neck of said assembly;
wherein one of the sheath means not containing said adhesive being adapted to be removably attached to said assembly, said one sheath means being removed from said assembly prior to using the assembly, the other sheath means containing said adhesive being adapted to be inserted to first engage said sealing means with said needle to thereby break said sealing means, said guard means being further inserted to permit said luer lock and said neck to engage said engaging means, said sheath means and said engaging means permitting said adhesive to flow into said engaging means when said assembly is fully inserted into said guard, thereby locking said guard means to said assembly when said adhesive cures and rendering said assembly immediately inoperative and also preventing an inadvertent needle puncture.

13. A needle guard means according to claim 12, wherein said assembly is completely rendered inoperative by pulling said plunger to draw adhesive in the chamber immediately after capping said guard means on the needle, luer lock, and neck of the assembly, said plunger being pushed thereafter to contact said plunger with said adhesive, whereby said adhesive permanently adhering said needle guard means to the exterior surface of said luer lock and said neck, said luer lock to said neck, and said plunger to said syringe body while filling the space in said needle with said adhesive, thereby permanently adhering all operative parts of said assembly to render said assembly completely inoperative.

14. A needle guard means according to claim 12 or 13, wherein said sheath means containing said adhesive further comprising an enlarged flange means adjacent said engaging means for preventing an accidental needle puncture to the user's hand when manually inserting said needle to said guard means.

15. A needle guard means according to claim 12 or 13, wherein said adhesive is colored to visually indicate flow of said adhesive.

16. A needle guard means according to claim 14, wherein said adhesive is colored to visually indicate flow of said adhesive.

17. A needle guard means according to claim 12 or 13, wherein each said engaging means having a lip means adjacent said opening end, which enables seating of said sealing means thereon.

18. A needle guard means according to claim 12 or 13, wherein said two sheath means being integral and juxtaposed side-by-side so that the opening end for each sheath means faces in the opposite directions.

* * * * *